United States Patent [19]

Skuballa et al.

[11] Patent Number: 5,013,758
[45] Date of Patent: May 7, 1991

[54] NOVEL CARBACYCLINS, PROCESSES FOR THEIR PREPARATION AND THEIR USE AS MEDICINAL AGENTS

[75] Inventors: Werner Skuballa; Bernd Raduechel; Helmut Vorbrueggen; Claus-Steffen Stuerzebecher; Martin Haberey; Ekkehard Schillinger, all of Berlin; Michael H. Town, Iffeldorf, all of Fed. Rep. of Germany

[73] Assignee: Schering Aktiengesellschaft, Berlin and Bergkamen, Fed. Rep. of Germany

[21] Appl. No.: 434,561

[22] Filed: Nov. 13, 1989

Related U.S. Application Data

[63] Continuation of Ser. No. 242,983, Sep. 12, 1988, abandoned, which is a continuation of Ser. No. 803,453, Nov. 29, 1985, abandoned, which is a continuation of Ser. No. 581,851, Feb. 21, 1984, abandoned.

[30] Foreign Application Priority Data

Feb. 18, 1983 [DE] Fed. Rep. of Germany ....... 3306123

[51] Int. Cl.$^5$ ............................................. A61K 31/19
[52] U.S. Cl. ................................... 514/573; 562/501
[58] Field of Search ........................ 562/501; 514/573

[56] References Cited

U.S. PATENT DOCUMENTS 4,423,067 12/1983 Skuballa ............................. 514/63

FOREIGN PATENT DOCUMENTS 69692 1/1983 European Pat. Off. .

Primary Examiner—Michael L. Shippen
Attorney, Agent, or Firm—Millen, White & Zelano

[57] ABSTRACT

(5E)-13,14,18,18,19,19-hexadehydro-3-oxa-6a-carba-prostaglandin $I_2$ derivatives of Formula I

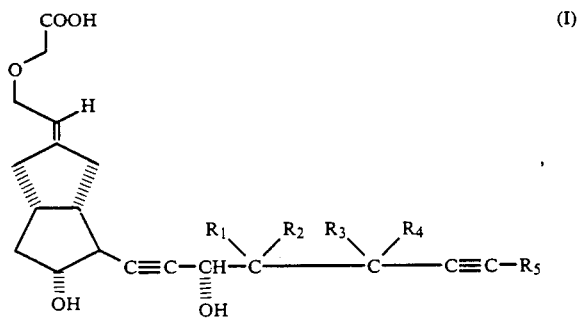

wherein
$R_1$, $R_2$, $R_3$, $R_4$ are hydrogen or alkyl of 1–5 carbon atoms, and
$R_5$ is an alkyl group of 1–5 carbon atoms, as well as the physiologically compatible salts thereof;
have pharmacologically valuable activity.

20 Claims, No Drawings

NOVEL CARBACYCLINS, PROCESSES FOR THEIR PREPARATION AND THEIR USE AS MEDICINAL AGENTS

This is a continuation of application Ser. No. 07/242,983 filed Sept. 12, 1988, now abandoned, which is a continuation of application Ser. No. 06/603,453 filed Nov. 29, 1985, now abandoned, which is a continuation of application Ser. No. 06/581,851 filed Feb. 21, 1984.

BACKGROUND OF THE INVENTION

The present invention concerns (5E)-13,14,18,18,19,19-hexadehydro-3-oxa-6o-carbaprostaglandin $I_2$ derivatives, the physiologically compatible salts thereof, a process for their preparation and their use as pharmaceuticals.

U.S. Pat. No. 4,423,067, whose disclosure is incorporated by reference herein, and corresponding German Unexamined Laid-Open Application 3,048,906.6, disclose carbacyclin derivatives of the formula

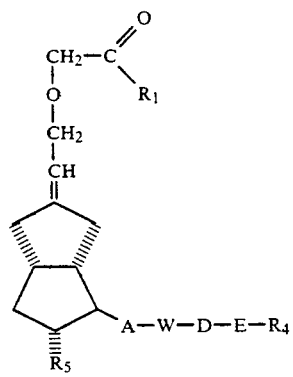

wherein
$R_1$ is $OR_2$ wherein $R_2$ is hydrogen, alkyl, cycloalkyl, aryl, or a heterocyclic residue; or is $NHR_3$ wherein $R_3$ is an acid residue or a hydrogen atom,
A is a $-CH_2-CH_2-$, trans-$CH=CH-$, or $-C\equiv C-$group,
W is a free or functionally modified hydroxymethylene group or a free or functionally modified

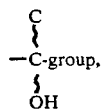

wherein the OH-group can be in the $\alpha$- or $\beta$-position,
D is a straight-chain or branched, saturated or unsaturated alkylene group of 1-10 carbon atoms which can optionally be substituted by fluorine atoms, 1,2-methylene or 1,1-trimethylene;
E is a $-C\equiv C-$bond or a $-CR_6=CR_7$-group wherein $R_6$ and $R_7$ are different from each other and are hydrogen or an alkyl group of 1-5 carbon atoms,
$R_4$ is an alkyl, cycloalkyl, or optionally substituted aryl group, or a heterocyclic group,
$R_5$ is a free or functionally modified hydroxy group, and when $R_2$ is hydrogen, the salts thereof with physiologically compatible bases These compounds exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; utilizability for treatment of stroke, prophylaxis and therapy of coronary heart disease, coronary thrombosis, cardiac infarction, peripheral arterial diseases, arteriosclerosis and thrombosis, therapy for shock, inhibition of bronchoconstriction, inhibition of gastric acid secretion, and cytoprotection for gastric and intestinal mucosa; antiallergic properties, lowering of pulmonary vascular resistance and pulmonary blood pressure, promotion of kidney blood flow, utilization in place of heparin or as an adjuvant in dialysis of hemofiltration, preservatron of blood plasma stores, especially blood platelet supplies, inhibition of labor, treatment of gestational toxicosis, enhancement of cerebral blood flow, etc. Furthermore, the novel prostaglandin analogs exhibit antiproliferative properties.

The nomenclature of these compounds is based on a proposal by Morton and Brokaw (J. Org. Chem. 44 : 2280 [1979]). Accordingly, (5E)-6a-carbaprostaglandin $I_2$ has the following structural formula:

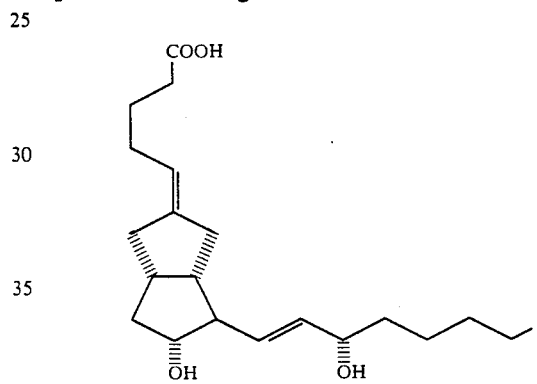

SUMMARY OF THE INVENTION

It is an object of this invention to provide new compounds having valuable pharmacological properties Upon further study of the specification and appended claims, further objects and advantages of this invention will become apparent to those skilled in the art.

These objects have been attained by providing (5E)-13,14,18,18,19,19-hexadehydro-3-oxa-6a-carbaprostaglandin $I_2$ derivatives of Formula I

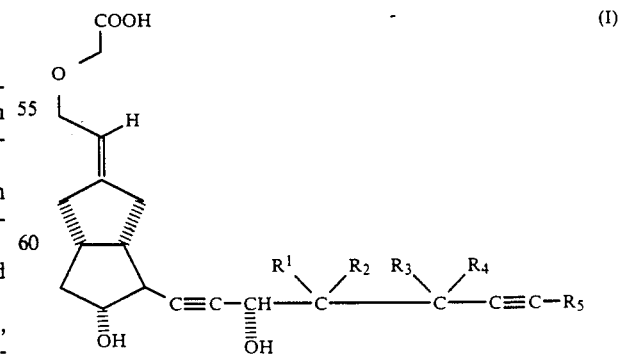

wherein
$R_1$, $R_2$, $R_3$, $R_4$ each independently are hydrogen or $C_{1-5}$-alkyl and $R_5$ is $C_{1-5}$-alkyl,
and physiologically compatible salts thereof with bases.

DETAILED DISCUSSION

Among the compounds of the U.S. patent and DOS, the (5E)-13,14,18,18,19,19-hexahydro-3-oxa-6a-carbaprostaglandin $I_2$ compounds of this invention show such outstanding properties as hypotensors and thrombocyte aggregation inhibitors that the necessary dosage can be significantly reduced further beyond the lowering achieved by the compounds of these references, whereby undesirable side effects are even more strongly suppressed. These (5E)-13,14,18,18,19,19-hexahydro-3-oxa-6a-carbaprostaglandin $I_2$ compounds are not described by name in DOS 3,048,906.6 or the corresponding U.S. patent. Compounds with A as a —C≡C— group are not extolled over the other compounds wherein A is a —CH$_2$—CH$_2$— or trans—CH═CH— group.

Suitable alkyl groups $R_1$, $R_2$, $R_3$, $R_4$, $R_5$ include straight-chain and branched alkyl residues of 1–5 carbon atoms, for example, methyl, ethyl, propyl, butyl, isopropyl, pentyl, etc. Preferred are methyl, ethyl, propyl and isopropyl, especially methyl and ethyl Inorganic and organic bases are suitable for salt formation, as known to those skilled in the art for the production of physiologically compatible salts. Examples include alkli metal hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)-methylamine, etc.

The invention furthermore relates to a process for the preparation of the prostacyclin derivatives of this invention of Formula I and their salts, comprising conventionally etherifying, in the presence of a base, a compound of Formula II

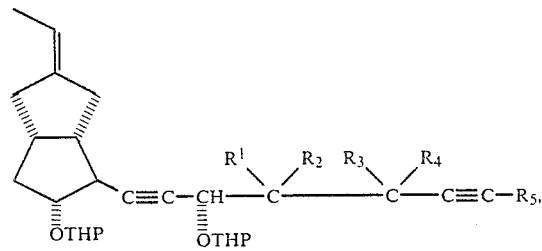

wherein
$R_1$, $R_2$, $R_3$, $R_4$, $R_5$ are as defined above and
THP is tetrahydropyranyl, with a haloacetic acid derivative of Formula III

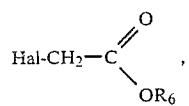

wherein
Hal is a chlorine, bromine, or iodine atom and
$R_6$ is $C_{1-4}$ alkyl or trialkylsilyl with $C_1C_4$ alkyl groups, or an alkali metal (Na, Li, K) cation, and, optionally, subsequently, in any desired sequence, conventionally separating isomers, saponifying esters, conventionally splitting off blocking groups, and, if desired, conventionally convertting the carboxy group into a physiologically compatible salt with a physiologically compatible base.

The reaction of the compound of Formula II with a haloacetic acid derivative of Formula III is conducted at temperatures of 0° C. to 100° C., preferably 10–80° C., in an aprotic solvent or solvent mixture, for example dimethyl sulfoxide, dimethylformamide, tetrahydrofuran, etc. Suitable bases to be used are those known to persons skilled in the art for etherifications, for example, sodium hydride, potassium tert-butylate, butyllithium, etc.

The saponification of the carbacyclin esters is effected by means of methods known to those skilled in the art, for example, with alkaline catalysts.

Blocking groups can be split off in an aqueous solution of an organic acid, for example, acetic acid, propionic acid, and others, or in an aqueous solution of an inorganic acid, for example, hydrochloric acid. To improve solubility, a water-miscible, inert organic solvent is suitably added. Organic solvents that can be used include, for example, alcohols, such as methanol and ethanol, and ethers, such as dimethoxyethane, dioxane, and tetrahydrofuran. Tetrahydrofuran is preferably used. The splitting-off step is preferably conducted at temperatures of 20° C. to 80° C.

The carboxylic acids of Foraula I can be converted into salts with suitable amounts of the corresponding inorganic bases under conventional neutralization conditions. For example, when dissolving the corresponding acids in water containing the stoichiometric amount of the base, the solid inorganic salt is obtained after evaporation of the water or after adding a water-miscible solvent, e.g., alcohol or acetone. For the production of an amine (organic) salt, the PG acid can be dissolved in a suitable solvent, e.g., ethanol, acetone, diethyl ether, or benzene, and at least the stoichiometric quantity of the amine is added to this solution. In this case, the salt is ordinarily obtained in the solid form or is isolated conventionally after evaporation of the solvent.

The starting materials of Formula II can be prepared, for example, by conventionally reacting an aldehyde of Formula IV (DOS 2,845,770, whose disclosure is incorporated by reference herein):

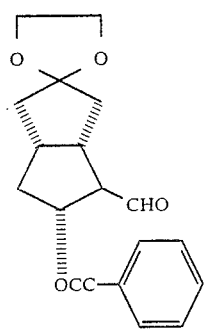

with a phosphonate of Formula V

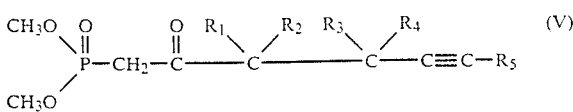

wherein $R_1$, $R_2$, $R_3$, $R_4$ and $R_5$ are as defined above, in the presence of a deprotonating agent, for example, sodium hydride or potassium tert-butylate, and of a brominating t, such as, for example, N-bromosuccinimide, to form a a ketone of Formula VI

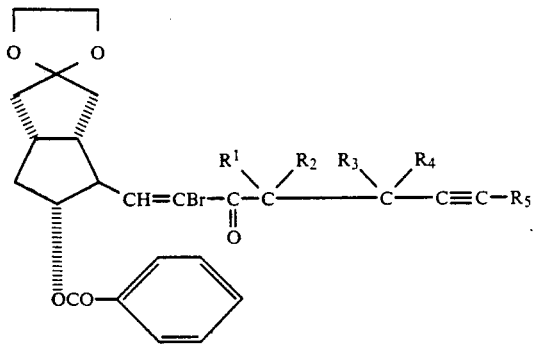
(VI)

and optionally subsequently separating diastereomers.

After conventional reduction of the keto group with sodium borohydride and optional separation of diastereomers; conventional saponification of the ester group, for instance with potassium carbonate, and, optionally, separation of diastereomers; conventional esterification with dihydropyran; and subsequent conventional splitting off of hydrogen bromide with, for example, potassium tert-butylate in dimethyl sulfoxide, the acetylene compound of Formula VII is obtained

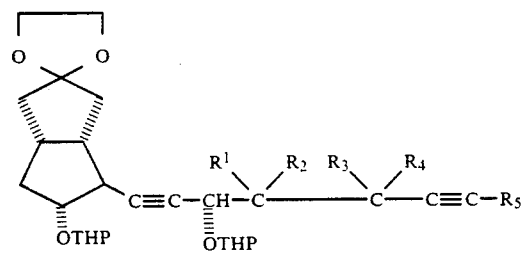
(VII)

Treatment with aqueous acetic acid, as well as optional separation of diastereomers, and subsequent etherification with dihydropyran yield the ketone of Formula VIII

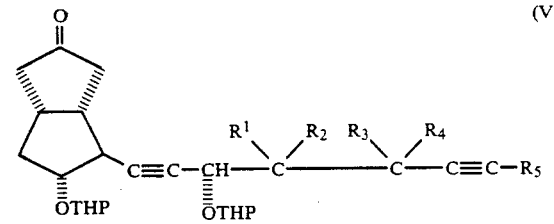
(VIII)

After an olefin-forming reaction with phosphonoacetic acid triethyl ester or phosphonoacetic acid trimethyl ester, reduction with lithium aluminum hydride, and subsequent separation of double-bond isomers, the compounds of Formula II are obtained, see also U.S. Pat. No. 4,423,067.

The phosphonates of Formula V can also be prepared in a manner known per se, e.g., by reacting an alkyl halogenide (producible from the corresponding alcohol by halogenation) of Formula IX.

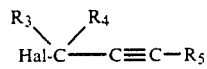
(IX)

with the dianion conventionally produced from the phosphonate of Formula X

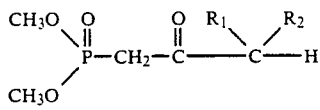
(X)

wherein $R_1$, $R_2$, $R_3$, $R_4$ and $R_5$ have the meanings given above.

The phosphonates of Formula V are furthermore accessible by reacting the anion of the dimethyl ester of methyl-phosphonic acid with an ester of Formula XI

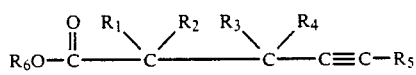
(XI)

wherein
$R_1$, $R_2$, $R_3$, $R_4$, and $R_5$ are as defined above and
$R_6$ is an alkyl group of 1-5 carbon atoms.
This ester can be conventionally obtained from the corresponding malonic acid ester by alkylation with the halogenide of Formula IX and subsequent decarbalkoxylation The ester of Formula XI is also conventionally obtainable from the carboxylic acid of Formula XII

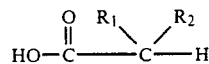
(XII)

wherein $R_1$ and $R_2$ are as defined above, by alkylation with the halogenide of Formula IX and subsequent esterification.

Concerning the preparation and also the use of the compounds of this invention, see also U.S. Pat. No. 4,423,067.

The compounds of this invention have blood-pressure-lowering and bronchodilatory effects They are furthermore suitable for inhibiting thrombocyte aggregation Consequently, the novel prostacyclin derivatives of Formula I represent valuable pharmaceutically active agents. Moreover, with a similar spectrum of activity, they exhibit a higher specificity as compared with corresponding prostaglandins and, above all, a substantially longer efficacy As compared with $PGI_2$, they are distinguished by higher stability. The high tissue specificity of the novel prostaglandins can be demonstrated in a study on smooth-muscle organs, for example, on the guinea pig ileum or on the isolated rabbit trachea, where a substantially lower stimulation can be observed than in the administration of natural prostaglandins of the E-, A-, of F-type.

The novel carbacyclin derivatives exhibit the properties typical for prostacyclins, in mammals, including humans, for example, lowering of peripheral arterial and coronary vascular resistance, inhibition of thrombocyte aggregation and dissolution of platelet thrombi, myocardial cytoprotection and thus lowering of systemic blood pressure without s:multaneously lowering stroke volume and coronary blood flow; utility in treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas; antiallergic properties, lowering of pulmonary vascular resistance and pulmonary blood pressure, promotion of kidney blood flow, utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. In addition, the novel carbacyclin derivatives exhibit antiproliferative properties. The carbacyclins of this invention also can be utilized in combination, for example, with β-blockers or diuretics The dosage of the compounds in these uses is generally 1–1,500 μg/kg/day, if administered to human patients The unit dosage for the pharmaceutically acceptable carrier is usually 0.01–100 mg.

Upon intravenous injection administered to nonanesthetized, hypertonic rats in doses of 5, 20, and 100 μg/kg body weight, the compounds of this invention exhibit a stronger blood-pressure-lowering effect and a more prolonged duration of efficacy than $PGE_2$ and $PGA_2$ without triggering diarrhea, as does $PGE_2$, or cardiac arrhythmias, as does $PGA_2$.

Upon intravenous injection administered to narcotized rabbits, the compounds of this invention show, as compared with $PGE_2$ and $PGA_2$, a stronger and also considerably prolonged blood-pressure-lowering effect without affecting other smooth-muscle organs or organ functions Sterile, injectable, aqueous or oily solutions are used for parenteral administration. Suitable for oral administration are, for example, tablets, dragees, or capsules.

The invention accordingly also concerns medicinal agents based on the compounds of general Formula I and conventional auxiliary agents and excipients.

The active agents of this invention are to serve, in conjunction with the excipients known and customary in galenic pharmacy, for example for the preparation of blood-pressure-lowering agents. For example, the compounds are active as antihypertensives, as hypotonies, of for both purposes.

In general, the administration of the compounds of this invention is analogous to that of the known agents Prostacyclin ($PGI_2$) and Ciloprost (INN of a new carbacyclin derivate described in U.S. Ser. No. 086,506 filed Oct. 19, 1979).

Each of the novel prostaglandin analogs of this invention is surprisingly and unexpectedly more useful than one cf the corresponding conventional prostaglandins or prostacyclins described above for at least one of the pharmacological purposes indicated above, because it has a different and narrower spectrum of biological potency than the known prostaglandins, and therefore is more specific in its activity and causes smaller and fewer undesired side effects than when the prostaglandin is used for the same purpose Moreover, because of its prolonged activity, fewer and smaller doses of the novel phostaglandin analogs are frequently effective in attaining the desired result Without further elaboration, it is believed that one skilled in the art can, using the preceding description, utilize the present invention to its fullest extent. The following preferred specific embodiments are, therefofe, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1
(5E)-(16S)-13,14-Didehydro-16,20-dimethyl-3-oxa-18,18,19,19-tetradehydro-6a-carbaprostaglandin $I_2$ A solution of 0.4 g of 2-[(E)-(1S, 5S, 6S, 7R)-7-(tetrahydropyran-2- n-2-yloxy) -6-[(3S, 4S)-4-methyl-3-(tetrahydro-pyran -2-yloxy)nona-1,6-diynyl]bicyclo[3.3.-0]octan-3-ylidene]-ethan-1-ol in 12 ml of tetrahydrofuran is combined with 80 mg of 55% strength sodium hydride suspension (in mineral oil), and the mixture is refluxed for one hour. A solution of 127 mg of bromoacetic acid in 4 ml of tetrahydrofuran is added, the mixture is refluxed for 18 hours, diluted with ether, and extracted four times under shaking with respectively 30 ml of 5% sodium hydroxide solution. This extract is adjusted to pH 3 with 10% sulfuric acid at 0° C., and extracted with methylene chloride. The organic extract is shaken with brine, dried over magnesium sulfate, and evaporated under vacuum, thus obtaining 220 mg of (5E)-(16S) -13,14-didehydro-16,20-dimethyl-3-oxa-18,18,19,19-tetradehydro -6a-carbaprostaglandin $I_2$ 11,15-bis(tetrahydropyranyl ether) which is stirred for 18 hours at 25° C. with 15 ml of acetic acid/water/tetrahydrofuran (65/35/10) to split off the blocking groups. The mixture is concentrated by evaporation with the addition of toluene, and the residue is chromatographed on silica gel with ethyl acetate/0.1–1% acetic acid, thus obtaining 145 mg of the title compound as a colorless oil.

IR ($CHCl_3$): 3600, 3400 (broad), 2930, 2223, 1730, 1600, 1425, 1380 $cm^{-1}$.

The starting material for the above title compound is prepared as follows:

(1a)
(1R,5S,6S,7R)-3,3-Ethylenedioxy-7-benzoyloxy-6-[(4S)-2-bromo-4-methyl-3-oxonon-1-en-6-ynyl]-bicyclo[3.3.0]octane At 0° C., a solution of 21.9 g of 3-methyl-2-oxooct-5-ynephosphonic acid dimethyl ester in 140 ml is added dropwise to a suspension of 3.57 g of sodium hydride (55% in mineral oil) in 360 ml of dimethoxyethane; the mixture is stirred for one hour at 0° C., and then 14.56 g of finely pulverized N-bromosuccinimide is added thereto. The mixture is agitated for one hour at 0° C., combined with a solution of 22.5 g of (1R,5S,6R,7R)-3,3-ethylene- dioxy-7-benzoyloxy-6-formylbicyclo[3.3.-0]octane in 180 ml of dimethoxyethane, and the mixture is stirred for 4 hours at 0° C. The reaction mixture is diluted with 3 1 of ether, washed neutral with brine, dried with sodium sulfate, and evaporated under vacuum. The residue is chromatographed with hexane/ether as the eluent on silica gel. After chromatographing the respective diastereomeric mixed fractions thre times, the more polar compound produced is 8.1 g of (1R,5S,6S,7R)-3,3-ethylenedioxy-7-benzoyloxy-6-[(4R)-2-bromo-4-methyl-3-3-oxonon-1-en-6-ynyl]bicyclo[3.3.0]octane and, as the less polar compound, 7.4 g of the title compound as colorless oils.

IR: 2935, 2878, 1715, 1690, 1601, 1595, 1450, 1270, 948 $cm^{-1}$.

(1b)
(1R,5S,6S,7R)-3,3-Ethylenedioxy-7-(tetrahydro-pyran-2-yloxy)-6-[(3S,4S)-2-bromo-4-methyl-3-(tetrahydropyran-2-yloxy)non-1-en-6-ynyl]-bicyclo [3.3.0]octane At −20° C., 3 g of sodium borohydride is added in incremental portions to a solution of 7.4 g of the ketone produced in Example (la) in 140 ml of methanol, and the mixture is agitated for 30 minutes at −20° C. The mixture is then diluted with ether, washed neutral with water, dried over magnesium sulfate, and evaporated under vacuum.

The crude product (15-epimer mixture) is dissolved in 300 ml of methanol, 2.95 g of potassium carbonate is added, and the mixture is stirred for 21 hours at 23° C. under argon. Then the mixture is concentrated under vacuum, diluted with ether, and washed neutral with brine, dried over magnesium sulfate, and evaporated under vacuum. Column chromatography on silica gel with ether/methylene chloride (7+3) yields first of all 2.6 g of the 15β-configured alcohol and, as the more polar component, 2.1 g of the 15α-configured alcohol (PG nomenclature) as colorless oils.

A solution of 2.1 g of the 15α-alcohol prepared as above, 20 mg of p-toluenesulfonic acid, and 1.4 g of dihydropyran in 50 ml of methylene chloride is agitated for 30 minutes at 0° C. Then the mixture is poured on dilute sodium bicarbonate solution, extracted with ether, washed neutral with water, dried over magnesium sulfate, and evaporated under vacuum. After chromatography of the residue on silica-gel, 2.6 g of the title compound is obtained as a colorless oil with hexane/ether (6+4).

IR: 2939, 2877, 1450, 969, 948 cm$^{-1}$.

(1c)
(1R,5S,6S,7R)-7-(Tetrahydropyran-2-yloxy)-6-(3S,4S)-4-methyl-3-(tetrahydropyran-2-yloxy)nona-1,6-diynyl]-bicyclo[3.3.0]octan-3-one A solution of 290 mg of the compound prepared according to Example (1b) in 2.5 ml of dimethyl sulfoxide and 1 ml of tetrahydrofuran is combined with 112 mg of potassium tert-butylate and the mixture is stirred for 2 hours at 23° C. The mixture is diluted with 10 ml of water and extracted three times with respectively 10 ml of ether/hexane (7+3). The extract is washed neutral with water, dried over brine, and evaporated under vacuum.

The residue is agitated for 22 hours with 15 ml of acetic acid/water/tetrahydrofuran (65/35/10), evaporated under vacuum with the addition of toluene, and the residue is purified by chromatography on silica gel. With ether, 150 mg of an oily compound is eluted which is reacted in 5 ml of dichloromethane with 140 mg of dihydropyran and 1 mg of ptoluenesulfonic acid at 0° C. After 30 minutes, the mixture is diluted with ether, extracted by shaking with 5% sodium bicarbonate solution and brine, dried over magnesium sulfate, and evaporated under vacuum. After chromatography of the residue on silica gel with hexane/ether (1+1), 185 mg of the title compound is obtained as a colorless oil.

IR:. 2940, 2876, 2216, 1738, 1020, 970 cm$^{-1}$.

(1d)
2-[(E)-(1S,5S,6S,7R)-7-(Tetrahydropyran-2-yloxy)-6-[(3S,4S)-4-methyl-3-(tetrahydropyran-2-yloxy)nona-1,6-diynyl]bicyclo[3.3.0]octan-3-ylidene]ethan-1-ol At 0° C., 225 mg of potassium tert-butylate is added to a solution of 529 mg of phosphonoacetic acid triethyl ester in 10 ml of tetrahydrofuran; the mixture is stirred for 10 minutes, combined with a solution of 0.6 g of the ketone produced according to Example (1c) in 6 ml of toluene, and agitated for 22 hours at 23° C. The mixture is diluted with 150 ml of ether, shaken once with water, once with 20% sodium hydroxide solution, washed neutral with water, dried over magnesium sulfate, and evaporated under vacuum. The residue is filtered with hexane/ether (6+4) over silica gel, thus obtaining 0.58 g of the unsaturated ester as a colorless oil.

IR: 2940, 2870, 2212, 1704, 1655, 970 cm$^{-1}$.

In incremental portions, 150 mg of lithium aluminum hydride is added at 0° C. to an agitated solution of 570 mg of the above-prepared ester in 25 ml of ether, and the mixture is stirred for 30 minutes at 0° C. The excess reagent is destroyed by dropwise addition of ethyl acetate, 1 ml of water is added, and the mixture is stirred for 3 hours at 20° C., filtered, and evaporated under vacuum. The residue is chromatographed with ether/hexane (3+2) on silica gel, thus obtaining as the less polar compound 140 mg of 2-[(Z)(1S, 5S,6S,7R)-7-(tetrahydropyran-2-yloxy)-6-[(3S,4S)-4-methyl-3-(tetrahydropyran-2-yloxy)nona-1,6-diynyl]bicyclo -[3.3.0]octan-3-ylidene]ethan-1-ol and 180 mg of the title compound as a colorless oil.

IR: 3620, 3450 (broad), 2940, 2860, 2212, 970 cm$^{-1}$.

EXAMPLE 2
(5E)-(16R)-13,14-Didehydro-16,20-dimethyl-3-oxa18,18,19,19-tetradehydro-6a -carbaprostaglandin I$_2$ In analogy to Example 1, 0.6 g of 2-[(E)-(1S,5S,6S,7R) -7-(tetrahydropyran-2-yloxy)-6-[(3S,4R)-4-methyl-3-(tetrahydro -pyran-2-yloxy)nona-1,6-diynyl]bicyclo[3.3.0]octan-3-ylidene]-ethan-1-ol yields 0.26 g of the title compound as a colorless oil.

IR: 3600, 3410 (broad), 2930, 2222, 1730, 1600, 1425, 1380 cm$^{-1}$.

The starting material for the above title compound is produced as follows:

(2a) (1R,5S,6S,7R)-3,3-Ethylenedioxy-7-(tetra-hydropyran-2-yloxy)-6-[(3S,4R)-2-bromo-4-methyl-3-(tetrahydropyran-2-yloxy)non-1-en-6-ynyl]bicyclo[3.3.-0]octane Analogously to Example (1b), 8 g of (1R,5S,6S,7R)-3,3-ethylenedioxy-7-benzoyloxy-6 -[(4R)-2-bromo-4-methyl-3-oxonon-1-en-6-ynyl]bicyclo[3.3.0]octane [polar 16-methyl diastereomer from Example (1a)]yields 2.9 g of the title compound as a colorless oil.

IR:- 2940, 2878, 1450, 970, 948 cm$^{-1}$.

(2b)
(1R,5S,6S,7R)-7-(Tetrahydropyran-2-yloxy)-6-[(3S,4R)-4-methyl-3-(tetrahydropyran-2-yloxy)nona-1,6-diynyl]bicyclo[3.3.0]octan-3-one In analogy to Example (1c), 2.8 g of the compound prepared according to Example (2a) yields 1.7 g of the title compound as a colorless oil.

IR: 2940, 2875, 2215, 1738, 1021, 970 cm$^{-1}$.

(2c)
2-[(E)-(1S,5S,6S,7R)-7-(Tetrahydropyran-2-yloxy)-6-[(3S,4R)-4-methyl-3-(tetrahydropyran-2-yloxy)nona-1,6-diynyl]bicyclo[3.3.0]octan-3-ylidene]ethan-1-ol Analogously to Example (1d), 1.6 g of the ketone produced according to Example (2b) yields, after chromatographic separation of isomers, 0.4 g of 2-[(Z)(1S,5S,6S,7R)-7-(tetrahydropyran-2-ylox-6-[(3S,4R)-4-methyl-3-(tetrahydropyran-2-yloxy)nona-16-diynyl]bicyclo -[3.3.0]octan-3-ylidene}ethan-1-ol and, as the more polar component, 0.5 g of the title compound as a colorless oil.

IR: 3600, 3440 (broad), 2942, 2860, 2212, 970 cm$^{-1}$.

EXAMPLE 3
(5E)-(16RS)-13,14-Didehydro-16-methyl-3-oxa-18,18,19,19-tetradehydro-6a-carbaprostaglandan I$_2$ In analogy to Example 1, 0.45 g of 2-[(E)(1S,5S,6S,7R)-7-(tetrahydropyran-2-yloxy)-6-[(3S,4RS)-4-methyl-3-(tetrahydropyran-2-yloxy)octa-1,6-diynyl]bicyclo -[3.3.0]octan-3-ylidene]ethane-1-ol yields 0.2 g of the title compound as a colorless oil.

IR: 3610, 3400 (broad), 2932, 2221, 1730, 1600 cm$^{-1}$.

The starting material for the above title compound is prepared as follows:

(3a) (1R,5S,6S,7R)-3,3-Ethylenedioxy-7-benzoyloxy-6-[(4RS)-2-bromo-4-methyl-3-oxooct-1-en-6-ynyl]bicyclo[3.3.0]octane At 0° C., a solution of 10.5 g of 3-methyl-2-oxohept-5-ynephosphonic acid dimethyl ester in 70 ml dimethoxyethane is added dropwise to a suspension of 1.81 g of sodium hydride in 180 ml of dimethoxyethane; the mixture is stirred for one hour at 0° C. and then 7.4 g of finely pulverized N-bromosuccinimide is added. The mixture is stirred for 30 minutes at 0° C., combined with a solution of 11.4 g of (1R,5S,6R,7R)-3,3-ethylenedioxy-7-benzoyloxy-6formylbicyclo [3.3.0]octane in 90 ml of dimethoxyethane, and agitated for 2 hours at 0° C. The reaction mixture is poured on saturated ammonium chloride solution and extracted with ether. The organic extract is washed neutral with water, dried over magnesium sulfate and evaporated under vacuum. After chromatographing the residue on silica gel, 8.2 g of the unsatura-ted ketone is obtained as a colorless oil with hexane/ether (3+2).

IR: 2930, 2880, 1712, 1688, 1602, 1595, 1450, 1275, 945 cm$^{-1}$.

(3b) (1R,5S,6S,7R)-3,3-Ethylenedioxy-7-(tetrahydro-pyran-2-yloxy)-6-[(3S,4RS)-2-bromo-4-methyl-3-(tetrahydropyran-2-yloxy)oct-1-en-6-ynyl]-bicyclo[3.3.0]octane At −40° C., 2.5 g of sodium borohydride is added in incremental portions to a solution of 5.9 g of the ketone prepared according to Example (3a) in 140 ml of methanol, and the mixture is stirred for 30 minutes at −40° C. Then the mixture is diluted with ether, washed neutral with water, dried over magnesium sulfate, and evaporated under vacuum. The crud product (mixture of 15-epimers) is dissolved in 200 ml of methanol; 2.5 g of potassium carbonate is added, and the mixture is stirred for 17 hours at 23° C. under argon. Thereafter the mixture is concentrated under vacuum, diluted with ether, and washed neutral with brine, then dried over magnesium sulfate, and evaporated under vacuum. Column chromatography on silica gel with ether/methylene chloride (7+3) yields initially 1.6.g of the 15β-configured alcohol, and as the more polar component, 2.1 g of the title compound (PG nomenclature 15α-hydroxy) as colorless oils. A solution of 1.6 g of the α-alcohol, 16 mg of p-toluenesulfonic acid, and 1.5 g of dihydropyran in 50 ml of methylene chloride is agitated for 35 minutes at 0° C. Subsequently the mixture is diluted with ether, shaken with dilute sodium carbonate solution, washed neutral with water, dried over magnesium sulfate, and evaporated under vacuum. Chromatography of the residue on silica gel yields, with hexane/ether (7+3), 2.17 g of the title compound as a colorless oil.

IR: 2940, 2870, 1450, 1120, 1018, 965, 948 cm$^{-1}$.

(3c) (1R,5S,6S,7R)-7-(Tetrahydropyran-2-yloxy)-6-[(3S,4RS)-4-methyl-3-(tetrahydropyran-2-yloxy)octa-1,6-diynyl]bicyclo[3.3.0]octan-3-one A solution of 2.30 g of the compound prepared according to Example (3b) in 23 ml of dimethyl sulfoxide and 10 ml of tetrahydrofuran is combined with 667 mg of potassium tert-butylate and agitated for 2 hours at 20° C. The mixture is diluted with 100 ml of water and extracted three times with respectively 100 ml of ether/hexane (8+2), the extract is washed with respectively 30 ml of water and brine, dried over magnesium sulfate, and evaporated under vacuum. The residue is stirred for 22 hours with 75 ml of acetic acid/water/tetrahydrofuran (65/35/10), evaporated under vacuum, and the remainder is purified by chromatography on silica gel. With ether, 1.05 g of an oily compound is eluted which is reacted in 40 ml of dichloromethane with 0.91 g of dihydropyran and 10 mg of p-toluenesulfonic acid at 0° C. After 30 minutes, the mixture is diluted with ether, shaken with sodium bicarbonate solution and brine, dried over magnesium sulfate, and evaporated under vacuum. Chromatography on silica gel with hexane/ether (1+1) yields 1.53 g of the title compound as a colorless oil.

IR: 2942, 2876, 2210, 1737, 1018, 970, 905, 868 cm$^{-1}$.

(3d) 2-[(E)-(1S,5S,6S,7R)-7-(Tetrahydropyran-2-yloxy)-6-[(3S,4RS)-methyl-3-(tetrahydropyran-2-yloxy)octa-1,6-diynyl]bicyclo[3.3.0]octan-3-ylidene]ethan-1-ol Analogously to Example (1d), 1.4 g of the ketone produced according to Example (3c) yields, after separation of isomers by chromatography, 0.37 g of 2-[(Z)(1S,5S,6S,7R)-7-(tetrahydropyran-2yloxy)-6-[(3S,4RS)-4-methyl -3-(tetrahydropyran-2-yloxy)octa-1,6-diynyl]bicyclo[3.3.0]octan-3-ylidene]ethan-1-ol and, as the more polar component, 0.48 g of the title compound as a colorless oil.

IR: 3600, 3420 (broad), 2945, 2860, 2225 cm$^{-1}$.

EXAMPLE 4
(5E)-(16S)-13,14-Didehydro-16,20-dimethyl-3-oxa-18,18,19,19-tetradehydro-6a-carbaprostaglandin I$_2$ Tris(hydroxymethyl)aminomethane Salt At 68° C., a solution of 15 mg of tris(hydroxymethyl)aminomethane in 0.05 ml of water is added to a solution of 55 mg of (5E)-(16S)-13,14-didehydro-16,20-dimethyl-3-oxa -18,18,19,19-tetradehydro-6a-carbaprostaglandin I$_2$ in 8 ml of acetonitrile. The mixture is allowed to cool under agitation, decanted from the solvent after 16 hours, and the residue is dried under vacuum, thus isolating 40 mg of the title compound as a viscous oil.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions

What is claimed is:

1. A (5E)-13,14,18,18,19,19-hexadehydro-3-oxa-6a-carbaprostaglandin $I_2$ of the formula

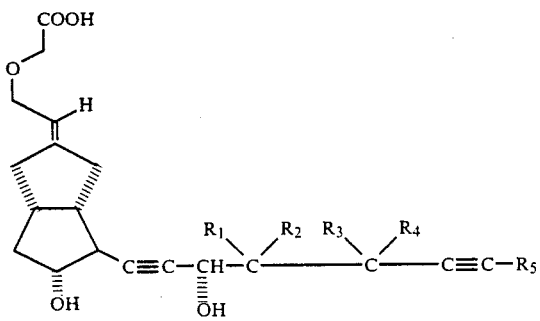

wherein $R_1$, $R_2$, $R_3$, and $R_4$ each independently is hydrogen or alkyl of 1–5 carbon atoms, and $R_5$ is alkyl of 1–5 carbon atoms, or a physiologically compatible salt thereof with a base.

2. A compound of claim 1, wherein $R_1$ is CH3.
3. A compound of claim 1, wherein $R_1$ and $R_5$ are $CH_3$.
4. A compound of claim 1, wherein $R_1$, $R_2$, $R_3$, $R_4$ and $R_5$ are each independently $CH_3$ or H.
5. (5E)-(16S)-13,14-didehydro-16,20-dimethyl-3-oxa-18,18,19,19-tetradehydro-6a-carbaprostaglandin $I_2$, a compound of claim 1.
6. (5E)-(16R)-13,14-didehydro-16,20-dimethyl-3-oxa-18,18,19,19-tetradehydro-6a-carbaprostaglandin $I_2$, a compound of claim 1.
7. (5E)-(16RS)-13,14-didehydro-16-methyl-3-oxa-18,18,19,19-tetradehydro-6a-carbaprostaglandin $I_2$, a compound of claim 1.
8. (5E)-(16S)-13,14-didehydro-16,20-dimethyl-3-oxa-18,18,19,19-tetradehydro-6a-carbaprostaglandin $I_2$ tris(hydroxymethyl)-aminomethane salt, a compound of claim 1.
9. A pharmaceutical composition comprising 0.01–100 mg of a compound of claim 1 and a pharmacologically acceptable carrier.
10. A pharmaceutical composition comprising an amount of a compound of claim 1 effective to lower blood pressure and a pharmacologically acceptable carrier.
11. A method of lowering blood pressure in a patient comprising administering an effective amount of a compound of claim 1 to the patient.
12. A compound of claim 1, wherein $R_5$ is $—C_2H_5$.
13. A compound of claim 1, wherein $R_1$ is $CH_3$ and $R_5$ is $—C_2H_5$.
14. A pharmaceutical composition comprising an effective amount of a compound of claim 1 and a pharmacologically acceptable carrier.
15. A method of inhibiting thrombocyte aggregation in a patient comprising administering an effective amount of a compound of claim 1.
16. A method of achieving a bronchodilatory effect in a patient comprising administering an effective amount of a compound of claim 1.
17. A method of treating hypertension in a patient comprising administering an effective amount of a compound of claim 1.
18. A compound of claim 1 wherein one of $R_1$ or $R_2$ is H and the other is alkyl.
19. A compound of claim 1, which is in the (16S)-configuration.
20. A compound of claim 1, which is in the (16R)-configuration.

* * * * *